United States Patent [19]

Mactaggart

[11] Patent Number: 4,565,444
[45] Date of Patent: Jan. 21, 1986

[54] ELECTRONICALLY SCANNED SPECTROMETER COLOR, BRIGHTNESS AND OPACITY MEASUREMENT AND CONTROL SYSTEM

[75] Inventor: John W. Mactaggart, Bolton, Canada

[73] Assignee: Sentrol Systems Ltd., Downsview, Canada

[21] Appl. No.: 438,004

[22] Filed: Nov. 1, 1982

[51] Int. Cl.$^4$ .............................................. G01J 3/51
[52] U.S. Cl. ...................................... 356/73; 356/418
[58] Field of Search ................. 356/73, 402, 405, 406, 356/408, 418, 419, 429, 430; 250/227; 350/96.24

[56] References Cited

U.S. PATENT DOCUMENTS

| | | | |
|---|---|---|---|
| 2,892,951 | 6/1959 | Linderman | 356/430 X |
| 3,206,606 | 9/1965 | Burgo et al. | 356/430 X |
| 3,806,256 | 4/1974 | Ishak | 356/405 X |
| 3,835,332 | 9/1974 | Bridges | 356/430 X |
| 3,896,730 | 4/1974 | Tirkkonen et al. | 250/341 |
| 3,936,189 | 2/1976 | DeRemigis | 356/405 X |
| 3,977,762 | 8/1976 | Sandbank | 350/96.24 |
| 4,019,819 | 4/1977 | Lodzinski | 356/73 |
| 4,029,419 | 6/1977 | Schumann et al. | 356/173 |
| 4,222,064 | 9/1980 | Lodzinski | 356/73 |
| 4,439,038 | 3/1984 | Mactaggart | 356/408 |

OTHER PUBLICATIONS

Tirkkonen et al., "A new infra-red absorption method for the measurement of paper web composition," Paper, Oct. 4, 1972, pp. 554–558.

Primary Examiner—Vincent P. McGraw
Assistant Examiner—S. A. Turner
Attorney, Agent, or Firm—Shenier & O'Connor

[57] ABSTRACT

Apparatus for measuring the color, brightness and opacity of a moving web in which light from a plurality of sources is directed towards and through a moving web. Light reflected from the surface of the web is conveyed by a plurality of light pipes to a first photodetector array located at a point remote from the web. A circular variable bandpass filter varies the wavelength of the radiation reaching the detector substantially continuously through the optical spectrum to produce a detector output which periodically scans the optical spectrum. The detector outputs at various wavelengths are weighted by a microcomputer to produce brightness and X, Y and Z tristimulus values. Light transmitted through the web is conveyed by a plurality of light pipes to a second photodetector array also located at a point remote from the web. The photodetector is also monitored by the microcomputer to provide an indication of the opacity of the web.

20 Claims, 5 Drawing Figures

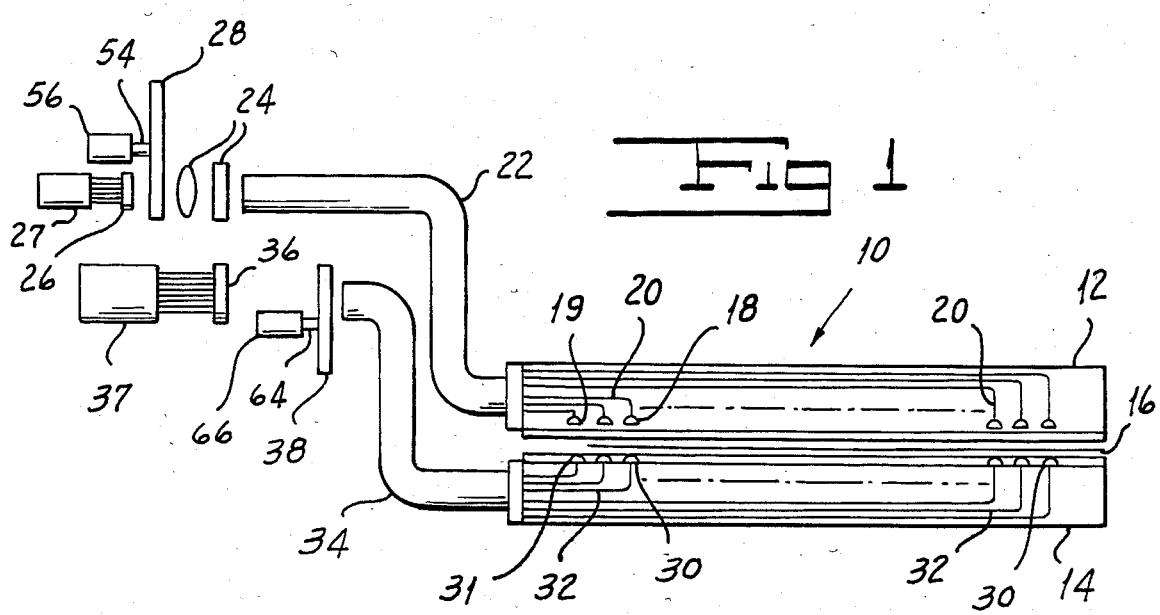
Fig. 1
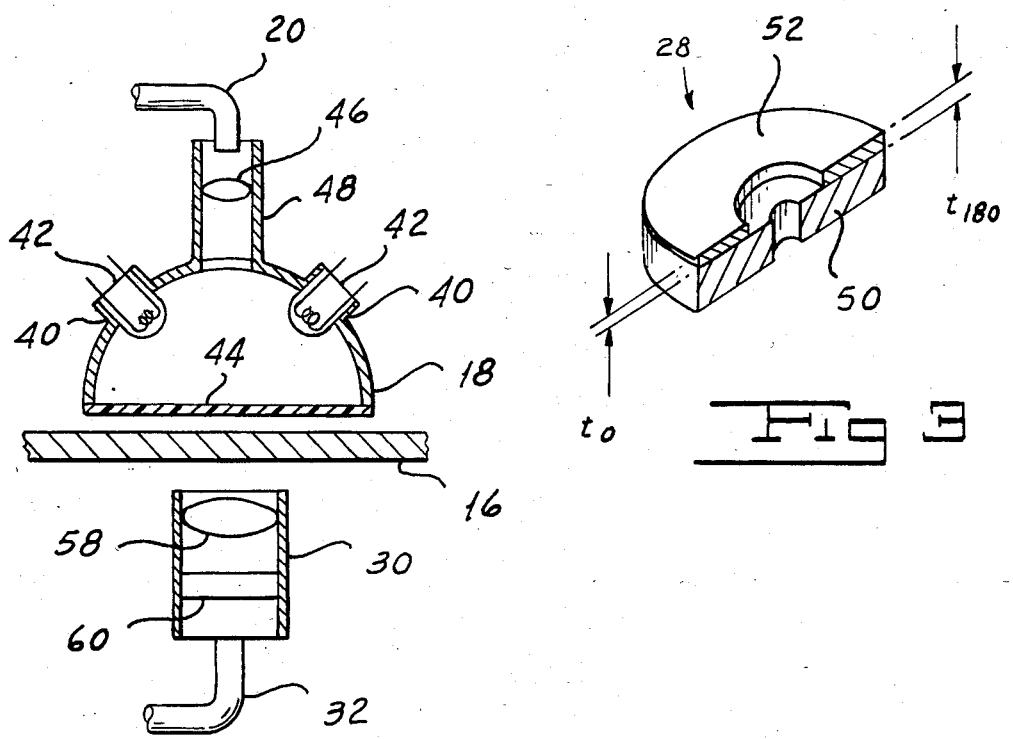
Fig. 2
Fig. 3

4,565,444

ELECTRONICALLY SCANNED SPECTROMETER COLOR, BRIGHTNESS AND OPACITY MEASUREMENT AND CONTROL SYSTEM

FIELD OF THE INVENTION

My invention relates to measuring and controlling the color, brightness and opacity of a moving web and more particularly, to an electronically scanned color brightness and opacity measurement system.

BACKGROUND OF THE INVENTION

In general, systems of the prior art for measuring and controlling the color of a moving web operate by measuring the tristimulus color coordinates X, Y and Z of light reflected from a moving portion of the web. One such system is described in De Remigis U.S. Pat. No. 3,936,189 in which multiple detectors using specially designed integrating filters simultaneously measure the tristimulus values, brightness and opacity.

In my copending application Ser. No. 240,171 filed Mar. 3, 1981, now U.S. Pat. No. 4,439,038 I disclose a color spectrometer system in which a single detector is used in conjunction with a circular variable bandpass filter to yield the tristimulus values. The filter is interposed in the optical path between the web and a detector and is rotated to produce a detector output which periodically scans the optical spectrum. While this system is generally satisfactory, it does not permit a fast scan color, brightness and opacity measurement as it uses only one detector which provides output related to only a small portion of the width of the moving web.

SUMMARY OF THE INVENTION

One object of my invention is to provide a rapid scan color, brightness and opacity measurement system especially adapted for multiple dye control.

Another object of my invention is to provide a color, brightness and opacity measurement and control system which permits the simultaneous standardization of a multiple detection system.

Still another object of my invention is to provide an electronically scanned spectrometer color, brightness and opacity measurement system for on-line analysis of paper quality.

A further object of my invention is to provide a color, brightness and opacity measurement and control system which permits opacity correction for individual frequencies.

A still further object of my invention is to provide a color, brightness and opacity measurement and control system which provides outputs over the entire width of the web.

Other and further objects of my invention will appear from the following description.

BRIEF DESCRIPTION OF THE DRAWINGS

In the accompanying drawings to which reference is made in the instant specification and in which like reference characters are used to indicate like parts in the various views:

FIG. 1 is a partly schematic view of my electronically scanned spectrometer color, brightness and opacity measurement and control system.

FIG. 2 is an enlarged view of one of the brightness and opacity detection units used in the system shown in FIG. 1, with parts shown in section.

FIG. 3 is a sectional perspective of the circular variable filter used in the measurement system shown in FIG. 1.

DESCRIPTION OF THE PREFERRED EMBODIMENT

Figure 4:
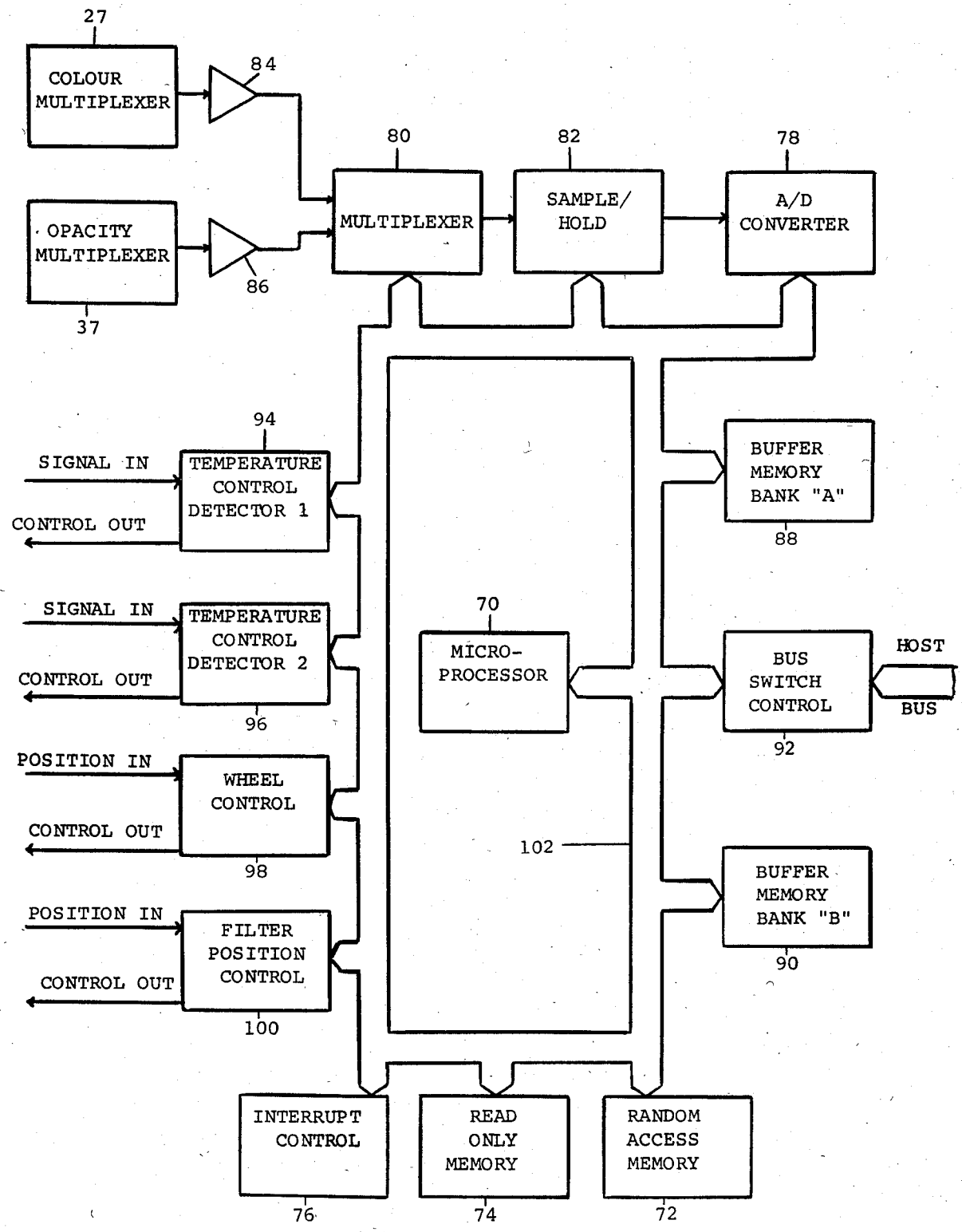
FIG. 4 is a block diagram of the microprocessor control system for use with the system shown in FIG. 1.

Referring now to FIG. 1, my electronically scanned spectrometer color brightness and opacity measurement and control system, indicated generally by the reference character 10, includes an upper sensor head 12 and a lower sensor head 14 positioned respectively above and below a web 16 moving in a direction perpendicular to the width of the paper. As will be more fully described hereinbelow, the upper sensor head is adapted to make a reflectance measurement for color and brightness and the lower sensor is adapted to make a transmission measurement for opacity.

The upper head 12 supports a plurality of hemispherical reflectors 18, arranged in a line extending across the width of the web in a direction perpendicular to web travel, such that each reflector registers with a portion of the width of the web. A plurality of low loss optical fiber pipes 20 connected at first ends thereof to respective reflectors 18 forms fiber optic bundle 22. As will be more fully described hereinbelow, bundle 22 leads to a location remote from web 16 at which radiation emanating from the bundle 22 is focused by collecting optics 24 onto a color photodetector array 26, through a circular variable disc filter 28.

The array 26 is made up of a plurality of individual photodetector elements, which may, for example, be silicon photodiodes, each adapted to receive radiation from a respective optical fiber pipe 20. As each pipe 20 of bundle 22 is associated with a single reflector 18, each detector element receives radiation reflected from a certain portion of the web. In addition, one detector element receives radiation from a reference reflector 19, which is located in an off-sheet position (away from the web). I connect the output of the array 26 to a multiplexer 27 adapted to feed the response of each photodetector element in the array to a microprocessor control system to be described hereinbelow.

The lower head 14 supports a plurality of tubular optical housings 30, arranged in a line extending across the width of the web in a direction perpendicular to web travel, such that each housing 30 registers with a portion of the width of the web. A plurality of low loss optical fiber pipes 32 on head 14 carry radiation away from the housings 30. Pipes 32 form a fiber optic bundle 34. As will be more fully described hereinbelow, radiation emanating from the bundle 34 is imaged onto an opacity photodetector array 36 through a standardization wheel 38.

The array 36 is also located at a point remote from the web and is made up of a plurality of individual photodetector elements, which may be silicon photodiodes, each adapted to receive radiation from a single fiber pipe 32. As each of the pipes 32 of bundle 34 is associated with a single housing 30, each detector element receives radiation transmitted through a certain portion of the web. In addition, one detector element of array 36 receives radiation from a reference housing 31, which is located in an off-sheet position. I connect the output of the array 36 to a multiplexer 37 adapted to supply the response of each photodetector element in the array to a microprocessor control system, to be described hereinbelow.

Referring now to FIG. 2, I have illustrated a single reflector 18 and housing 30, to which the others are identical, shown in operative position with respect to the web. The reflector 18 is formed with a pair of sockets 40 adapted to carry lamps 42. I coat the interior of each reflector 18 with barium sulphate to render it light integrating. While any suitable light source may be employed, preferably I use two quartz iodine lamps supplied by a constant current source for the lamps 42. Light deflectors or baffles, not shown, may be used to insure proper distribution of light from the sources within the reflector, while at the same time preventing the optic fiber 20 associated with the reflector 18 from being directly illuminated by the sources. Instead, light is directed through a quartz window 44 onto a portion of the web 16.

I form an opening in the upper portion of the reflector 18 through which reflected light from a spot portion of the web is directed to the open end of the associated optical pipe 20. More specifically, a collecting lens 46 disposed inside a tube 48 focuses light from the spot portion of the web onto the open end of the associated low loss optical fiber pipe 20. The fiber pipe 20 conducts the radiation along bundle 22 to optics 24 where it is focused through filter 28 onto a single element of the photodetector array 26.

As shown in FIG. 3, filter 28 comprises a substrate 50 having an interference filter coating 52 on one side thereof. In a manner known in the art, the thickness of the interference filter coating 52 on the substrate 50 varies with angular displacement about the axis of the filter 28. As a result, there is a corresponding angular dependence on the center wavelength that is passed by any particular angular segment of the filter coating 52. Thus, in the embodiment shown, the thickness $t_0$ of the thinnest, or 0°, segment coating is such as to pass a wavelength of about 400 nanometers, while the thickness of the 360° segment coating (not shown) is such as to pass a wavelength of about 800 nanometers. Between these two extremes, the thickness and hence pass band wavelength varies linearly with angular displacement. For example, the thickness $t_{180}$ of the 180° segment is such as to pass a wavelength of about 600 nanometers.

I mount filter 28 on the shaft 54 of a suitable motor such as a stepper motor 56 which rotates the filter 28 to vary the wavelength of the radiation transmitted to the detector array 26. A position encoder, not shown, may be coupled to the motor shaft 54 to provide a parallel digital output indicating the particular angular segment of the filter 28 that intercepts the optical axis. The filter 28 is interposed in the optical path and is rotated to produce a detector output which periodically scans the optical spectrum. As more fully described in my copending application, Ser. No. 240,171 filed Mar. 3, 1981 for a method and apparatus for measuring and controlling the color of a moving web, the detector outputs at the various wavelength are weighted to produce X, Y, and Z tristimulus values.

We position a respective collecting lens 58 in each housing 30 near that end adjacent to the web. The lens 58 is adapted to focus light transmitted through a spot portion of the web illuminated by lamps 42 onto the open end of the associated optical fiber pipe 30 through an opacity filter 60. The fiber pipe conducts the radiation through bundle 34, to be imaged onto a photodiode array 36 through the opacity standardization wheel 38. The opacity standard wheel is mounted on a shaft 64 of a suitable motor such as a stepper motor 66 which rotates the wheel at timed intervals to move a sample into the path of the radiation, for calibration of the detector.

Referring now to FIG. 4, one form of control arrangement which may be used in my electronically scanned spectrometer color, brightness and opacity measurement and regulating system includes a microprocessor 70 having a local scratch pad random access memory 72, a read only memory 74 for storage of the operating program and an interrupt control 76. The processor controls digitization of the incoming analog signals through an analog to digital converter 78 which receives analog signals from each element of both detection arrays 26 and 36 through a multiplexer 80 and a sample and hold amplifier 82. The multiplexer 80 is adapted to be operated by the microprocessor to transmit signals alternately from the color multiplexer 27 and from the opacity multiplexer 37 to the converter 78 through respective preamplifiers 84 and 86. The conversion values are stored in one of two buffer memory banks 88 and 90 by a slave processor or bus switch control 92.

In addition the processor 70 monitors and controls the temperature of the two photodetector arrays 26 and 36 through a pair of suitable temperature control units 94 and 96, monitors and controls the position of the opacity standard wheel 38 through a suitable control unit 98 and monitors and controls the position of the circular variable disc filter 28 through a suitable control unit 100. The microprocessor 70 communicates with each of the components of the control system through a local digital data bus 102.

Figure 5:
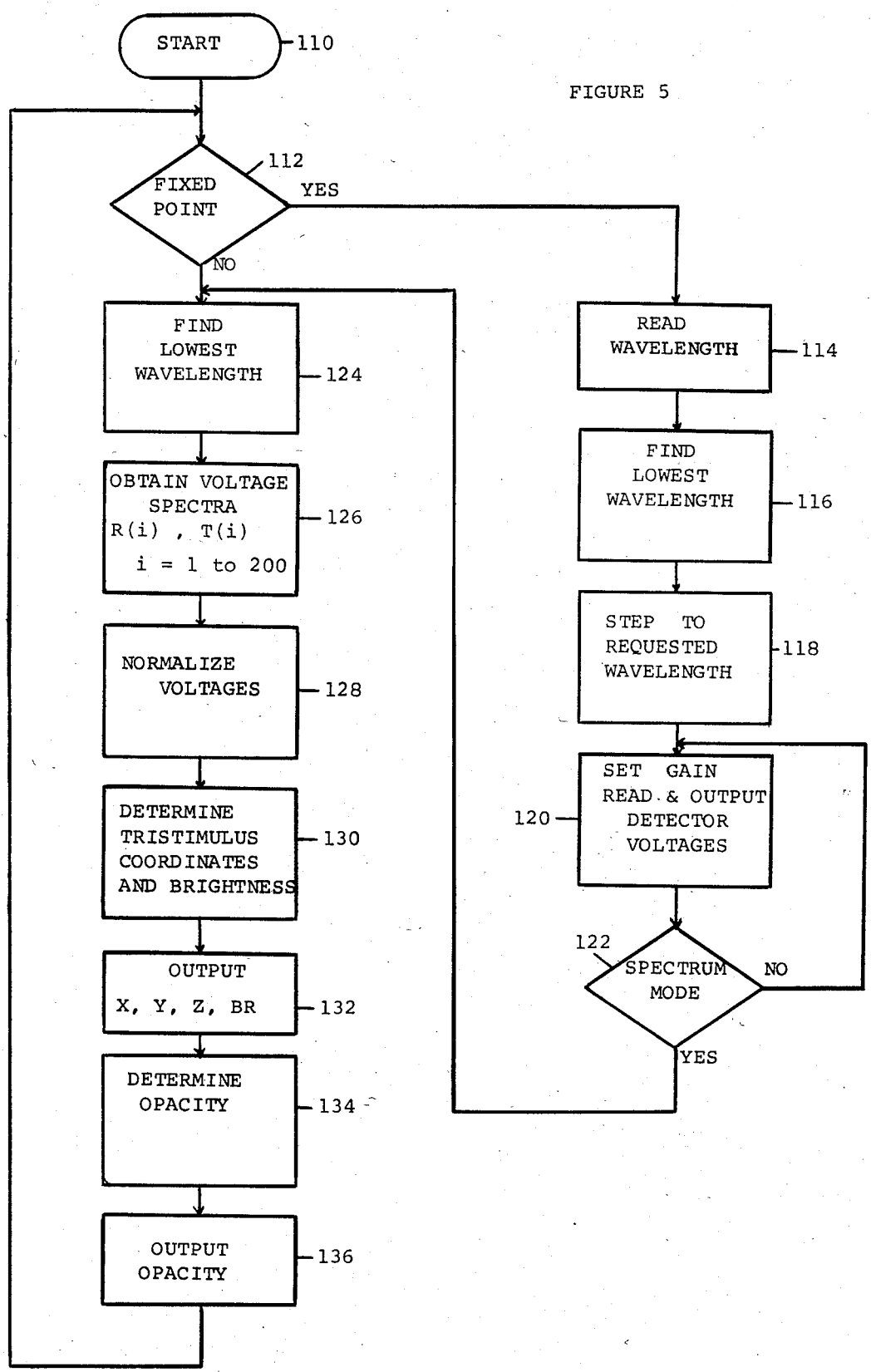
FIG. 5 is a flow chart of a program for controlling the operation of the system shown in FIG. 4.

Referring now to FIG. 5, the routine followed by microcomputer 70 begins at block 110. Initially a determination is made as to whether detector voltage outputs are to be obtained over an entire spectrum or for a specific (fixed) wavelength (block 112). If detector outputs are to be obtained for specific wavelengths, the filter position control unit 100 is interrogated to determine the present angular position of the filter wheel 28 and hence the wavelength of the radiation reaching the detector (blocks 114 and 116). The control unit 100 then operates the stepper motor 56 to rotate the filter wheel 28 such that radiation of the requested wavelength reaches the detector 26 (block 118). The gain of preamplifiers 84 and 86 is set and voltage outputs from the detectors 26 and 36, through their respective multiplexers 27 and 37 are read by the system and stored in one of the buffer memory banks 88 and 90 (block 120). The program can continue obtaining detector voltage outputs for a specific wavelength in which case it loops back to block 120, or it can enter the spectrum mode and proceed to block 124 (block 122).

In the spectrum mode the program measures the energy R(i) reflected from and the energy T(i) transmitted through the web 16 in terms of voltage outputs from the detectors 26 and 36 over a frequency spectrum expressed by wavelengths ranging from 400 nanometers (nm) to 800 nm, as provided by the filter wheel 28. Outputs from the detectors are collected beginning at the lowest wavelength, as determined by the filter position control unit 100, (block 124) and continuing as the filter wheel is stepped through the spectrum (block 126). Detector outputs are collected for every 2 nm change in wavelength between 400 nm and 800 nm, thereby yielding a 200 point measurement (i=1 to 200) for each scan of the spectrum.

The reflectance voltage outputs obtained R(i) are essentially "raw" voltage signals which must be converted to normalized voltage S(i) by use of the formula:

$$S(i) = \frac{R(i) - RB(i)}{RW(i) - RB(i)} \cdot \frac{1}{GR(i)} \quad (1)$$

where RB(i) is the output generated by the reflections of a black background at standardize time, RW(i) is the output generated by the reflections at a white standard at standardize time and 1/GR(i) is a normalizing function which compensates for the spectrums created by the lamps 42 (block 128).

The normalized reflectance voltage outputs S(i) or reflectance spectrum is then used to calculate the tristimulus color coordinates X, Y and Z and the brightness BR by comparing the reflectance outputs at specific wavelengths to the outputs over the total range of wavelengths. This is accomplished by use of the equations:

$$X = XX \cdot \Sigma_j S(j) \cdot f(x)[j] \quad (2)$$

$$Y = YY \cdot \Sigma_k S(k) \cdot f(y)[k] \quad (3)$$

$$Z = ZZ \cdot \Sigma_l S(l) \cdot f(z)[l] \quad (4)$$

$$BR = BB \cdot \Sigma_m S(m) \cdot f(b)[m] \quad (5)$$

wherein f(x), f(y), f(z) and f(b) are filter functions corresponding to the spectral regions associated with the tristimulus coordinates X, Y and Z, and the brightness BR (block 130). Once the values X, Y, Z and BR are determined, they are displayed in any suitable manner (block 132).

The program then determines opacity by the use of the transmission signal T(n) and the formula:

$$CO = \Sigma_n \frac{T(n) - TB(n)}{GT(n)} \cdot OP[n] \quad (6)$$

where TB(n) is the radiation transmitted from a standard background, 1/GT(n) is a normalizing function which compensates for the spectrum created by the lamps 42 and OP[n] is a filter function corresponding to the spectral region associated with opacity. The output CO of equation 6 is then normalized by the function:

$$OF = F(C0, C1, C2) \quad (7)$$

to give the opacity, which is then displayed (blocks 134 and 136). The program then loops back to block 112.

The generated X, Y and Z values can be fed directly to a computer set up to give the desired measurements and to control the production process in response to deviations of the measured values from the desired values, as more fully described in my copending application Ser. No. 240,171 filed Mar. 3, 1981.

It will be seen that I have accomplished the objects of my invention. I have provided a rapid scan color, brightness and opacity measurement system for multiple dye control which permits the simultaneous standardization of a multiple detection system. My electronically scanned spectrometer color, brightness and opacity measurement system permits on-line analysis of paper quality and opacity correction for individual frequencies.

It will be understood that certain features and subcombinations are of utility and may be employed without reference to other features and subcombinations. This is contemplated by and is within the scope of my claims. It is further obvious that various changes may be made in details within the scope of my claims without departing from the spirit of my invention. It is, therefore, to be understood that my invention is not to be limited to the specific details shown and described.

Having thus described my invention what I claim is:

1. Apparatus for obtaining a profile measurement of the color spectrum of a moving web including in combination means for illuminating a plurality of regions of said web, a corresponding plurality of photodetectors having respective light-collecting surfaces, a circular variable bandpass filter, means for directing light emanating from said regions along respective paths onto said light-collecting surfaces, said paths intersecting said filter along a radius thereof, and means for rotating said filter to vary the wavelength transmitted to said photodetectors.

2. Apparatus as in claim 1 in which said illuminating means comprises respective lamps disposed at spaced locations adjacent to said regions.

3. Apparatus as in claim 1 in which said regions are spaced across said web.

4. Apparatus as in claim 1 in which said photodetectors are spaced laterally from said web with reference to the direction of movement thereof.

5. Apparatus as in claim 1 in which said light-directing means comprises respective light pipes having first ends adjacent to said regions and second ends adjacent to said light-collecting surfaces, said second ends of said light pipes being so arranged relative to said light-collecting surfaces that each of said light pipes directs light on only one of said surfaces.

6. Apparatus as in claim 1 in which said light-directing means comprises respective light pipes having first ends adjacent to said regions and second ends forming a linear array along a radius of said filter, said second ends of said light pipes being so arranged relative to said light-collecting surfaces that each of said light pipes directs light on only one of said surfaces.

7. Apparatus as in claim 1 in which said light-directing means comprises respective light pipes having first ends adjacent to said regions and second ends forming a linear array along a radius of said filter, said light-collecting surfaces forming a linear array along said radius on the other side of said filter from said light pipes, said second ends of said light pipes being so arranged relative to said light-collecting surfaces that each of said light pipes directs light on only one of said surfaces.

8. Apparatus as in claim 1 in which said light-directing means comprises respective light pipes having first ends adjacent to said regions and second ends forming a linear array along a radius of said filter, said light-collecting surfaces forming a linear array along said radius on the other side of said filter from said light pipes, and means for forming an optical image of light emitted from said second ends of said light pipes on said surfaces, said second ends of said light pipes being so arranged relative to said light-collecting surfaces that each of said light pipes directs light on only one of said surfaces.

9. Apparatus as in claim 1 in which said light-directing means directs light reflected from said regions onto said light collecting surfaces.

10. Apparatus for obtaining a profile measurement of the color spectrum of a moving web including in combination a plurality of lamps arranged at spaced locations across said web, said lamps illuminating respective regions of said web spaced from one another, a corresponding plurality of photodetectors having respective light-collecting surfaces, means for directing light emanating from said regions along respective paths onto said light-collecting surfaces, an optical filter disposed in said paths, said filter transmitting an essentially monochromatic band of radiation of variable wavelength, and means for varying the wavelength of said filter to obtain said measurement of said web.

11. Apparatus as in claim 10 in which said filter is a circular variable filter, said means for varying said wavelength comprising means for rotating said filter.

12. Apparatus as in claim 10 further comprising respective reflectors corresponding to said lamps, said reflectors being arranged to reflect light from said lamps onto said regions.

13. Apparatus as in claim 10 further comprising respective concave reflectors corresponding to said lamps, said reflectors being arranged to reflect light from said lamps onto said regions.

14. Apparatus as in claim 10, further comprising respective concave reflectors corresponding to said lamps, said reflectors having diffusely reflective inner surfaces and being arranged to refect light from said lamps onto said regions.

15. Apparatus as in claim 10 in which said light-directing means directs light reflected from said regions onto said photoconductors.

16. Apparatus for obtaining a profile measurement of the color spectrum of a moving web including in combination means for illuminating a plurality of regions of said web, a variable-wavelength optical filter, said filter transmitting an essentially monochromatic band of radiation, respective light pipes having first ends receptive to light emanating from said regions and second ends disposed on one side of said filter, respective photodetectors having light-collecting surfaces, said surfaces being disposed on the other side of said filter from said light pipes, means for forming an optical image of light emitted from said second ends of said light pipes on said light-collecting surfaces, said second ends of said light pipes being so arranged relative to said light-collecting surfaces that each of said light pipes directs light on only one of said surfaces, and means for varying the wavelength of said filter to obtain said measurement of said web.

17. Apparatus as in claim 16 in which said filter is a circular variable filter, said means for varying said wavelength comprising means for rotating said filter.

18. Apparatus as in claim 16 in which said filter is a circular variable filter, said second ends of said light pipes being disposed along a radius of said filter.

19. Apparatus as in claim 16 in which said first ends of said light pipes are receptive to light reflected from said regions.

20. Apparatus for obtaining a profile measurement of the color spectrum of a moving web including in combination a plurality of lamps arranged at spaced locations across said web, said lamps illuminating respective regions of said web, a circular variable bandpass filter, respective light pipes having first ends receptive to light reflected from said regions and second ends forming a linear array along a radius of said filter on one side thereof, respective photodetectors having light-collecting surfaces, said surfaces forming a linear array along said radius on the other side of said filter from said light pipes, means for forming an optical image of light emitted from said second ends of said light pipes on said light-collecting surfaces, said second ends of said light pipes being so arranged relative to said light-collecting surfaces that each of said light pipes directs light on only one of said surfaces, and means for rotating said filter to vary the wavelength transmitted to said detectors.

* * * * *